(12) United States Patent
Hashimoto et al.

(10) Patent No.: US 7,858,210 B2
(45) Date of Patent: Dec. 28, 2010

(54) ELECTROLUMINESCENCE DEVICE

(75) Inventors: Masashi Hashimoto, Tokyo (JP); Satoshi Igawa, Fujisawa (JP); Takao Takiguchi, Chofu (JP)

(73) Assignee: Canon Kabushiki Kaisha, Tokyo (JP)

( * ) Notice: Subject to any disclaimer, the term of this patent is extended or adjusted under 35 U.S.C. 154(b) by 277 days.

(21) Appl. No.: 12/040,961

(22) Filed: Mar. 3, 2008

(65) Prior Publication Data
US 2008/0272692 A1    Nov. 6, 2008

(30) Foreign Application Priority Data
Mar. 13, 2007    (JP)    .............. 2007-063596

(51) Int. Cl.
*H01L 51/52*    (2006.01)
(52) U.S. Cl. ...................... 428/690; 313/504
(58) Field of Classification Search ............ 428/690
See application file for complete search history.

(56) References Cited

U.S. PATENT DOCUMENTS

| | | | | |
|---|---|---|---|---|
| 2005/0222417 | A1* | 10/2005 | Brown et al. ........... | 546/37 |
| 2006/0127698 | A1* | 6/2006 | Tokailin et al. ........ | 428/690 |
| 2007/0249878 | A1 | 10/2007 | Iwawaki et al. ........ | 585/27 |
| 2007/0252141 | A1 | 11/2007 | Negishi et al. ........ | 257/40 |

FOREIGN PATENT DOCUMENTS

| JP | 10-189247 | 7/1998 |
|---|---|---|
| JP | 11-176573 | 7/1999 |
| JP | 2002-069044 | 3/2002 |
| JP | 2005-235633 | 9/2005 |

OTHER PUBLICATIONS

Renge, I. J. Phys. Chem. A 2000, 104, 7452-7463.*

* cited by examiner

*Primary Examiner*—D. Lawrence Tarazano
*Assistant Examiner*—J. L. Yang
(74) *Attorney, Agent, or Firm*—Fitzpatrick, Cella, Harper & Scinto

(57) ABSTRACT

A layer is spaced between an anode and a cathode and is composed of an organic compound represented by the following general formula [1].

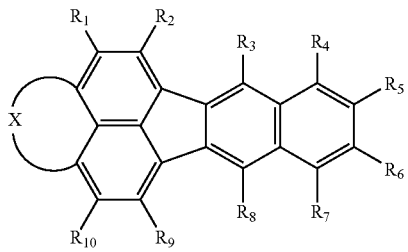

[1]

wherein $R_1$ to $R_{10}$ are each independently a hydrogen atom, a halogen atom, a substituted amino group, an alkyl group, an aryl group, and a heterocyclic group; and X represents (a) an alkylene group having 2 to 6 carbon atoms, wherein in the alkylene group, one or separate two methylene groups may be substituted by —O—, —CO—, —CO—O—, —S—, or —$NRa_1$—, and a hydrogen atom may be substituted by a linear, branched, or cyclic alkyl group having 1 to 10 carbon atoms, (b) an aryl group which may be substituted, or (c) a heterocyclic group which may be substituted, or (d) a fluorine atom.

4 Claims, 3 Drawing Sheets

ELECTROLUMINESCENCE DEVICE

BACKGROUND OF THE INVENTION

1. Field of the Invention

The present invention relates to a light-emitting device using an organic compound, and particularly to an organic light-emitting device including a layer which contains a compound having a specified molecular structure.

2. Description of the Related Art

In recent years, remarkable progress has been made in organic light-emitting devices. Organic light-emitting devices are characterized by high luminance at a low applied voltage, various emission wavelengths, high responsiveness, and are capable of being formed in thin and lightweight light-emitting devices. Therefore, there is the possibility of wide applications.

However, at present, light output with higher luminance or higher conversion efficiency is required. Also, there are many problems with durability, such as time-lapse change in long-term use, deterioration due to atmospheric gases including oxygen and humidity, and the like. Further, when applied to a full-color display, emission of blue, green, and red light, which is of high color purity, is required. However, these problems have not been sufficiently resolved.

Further, many aromatic compounds and condensed ring aromatic compounds have been investigated as fluorescent organic compounds used for luminescent layers. However, organic compounds with sufficient luminance and durability have not yet been uncovered.

Japanese Patent Laid-Open Nos. 2002-069044 and 10-189247 disclose that a compound containing a benzofluoranthene skeleton is applied to an organic light-emitting device in order to improve emission efficiency and luminance or to increase its life time (improving durability). Japanese Patent Laid-Open No. 2002-069044 discloses the application of a benzofluoranthene compound to organic light emission. Japanese Patent Laid-Open No. 10-189247 discloses the application of a benzo[k]fluoranthene compound to an organic light-emitting device. Japanese Patent Laid-Open No. 11-176573 discloses the application of a compound to an organic light-emitting device, the compound having an aromatic ring condensed at the 3- and 4-positions of a benzo[k]fluoranthene ring. Japanese Patent Laid-Open No. 2005-235633 discloses the application of a compound to an organic light-emitting device, the compound being crosslinked at the 3- and 4-positions of a benzo[k]fluoranthene ring through two nitrogen atoms.

In order to apply an organic light-emitting device to a display device such as a display, it is necessary to simultaneously secure high-luminance light output and high durability.

SUMMARY OF THE INVENTION

The present invention provides a light-emitting device having light output with high luminance and also provides a light-emitting device with high durability.

The present invention provides an organic light-emitting device including a pair of electrodes including an anode and a cathode, and a layer of an organic compound held between the pair of electrodes. The layer of the organic compound contains a compound represented by the following general formula [1]:

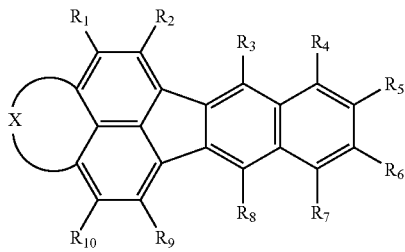

[1]

wherein $R_1$ to $R_{10}$ are each independently selected from a hydrogen atom, a halogen atom, a substituted amino group, a linear, branched, or cyclic alkyl group having 1 to 20 carbon atoms (in the alkyl group, one or at least two separate methylene groups may be substituted by —O— or —C=C—, and a hydrogen atom may be substituted by a fluorine atom), an aryl group which may have a substituent (the substituent is a halogen atom, a substituted amino group, or a linear, branched, or cyclic alkyl group having 1 to 20 carbon atoms (in the alkyl group, one or at least two separate methylene groups may be substituted by —O—, and a hydrogen atom may be substituted by a fluorine atom)), and a heterocyclic group which may have a substituent (the substituent is a halogen atom, a substituted amino group, or a linear, branched, or cyclic alkyl group having 1 to 20 carbon atoms (in the alkyl group, one or at least two separate methylene groups may be substituted by —O—, and a hydrogen atom may be substituted by a fluorine atom)); and X represents an alkylene group having 2 to 6 carbon atoms [in the alkylene group, one or separate two methylene groups may be substituted by —O—, —CO—, —CO—O—, —S—, or —NRa$_1$— (Ra$_1$ may be a hydrogen atom or substituted by a linear, branched, or cyclic alkyl group having 1 to 10 carbon atoms (in the alkyl group, a hydrogen atom may be substituted by a fluorine atom), and a hydrogen atom may be substituted by a linear, branched, or cyclic alkyl group having 1 to 10 carbon atoms (in the alkyl group, a hydrogen atom may be substituted by a fluorine atom), an aryl group which may be substituted, a heterocyclic group which may be substituted, or a fluorine atom].

In the organic light-emitting device, the layer composed of the organic compound may be a luminescent layer which may be composed of at least two compounds used as host and guest materials, and the compound represented by the general formula [1] is the guest material of the luminescent layer.

According to the present invention, an excellent light-emitting device capable of emitting light with high luminance and of maintaining high luminance for a long time can be obtained. Also, according to the present invention, a light-emitting device excellent as a display device can be obtained.

Further features of the present invention will become apparent from the following description of exemplary embodiments (with reference to the attached drawings).

DESCRIPTION OF THE EMBODIMENTS

Figure 1:
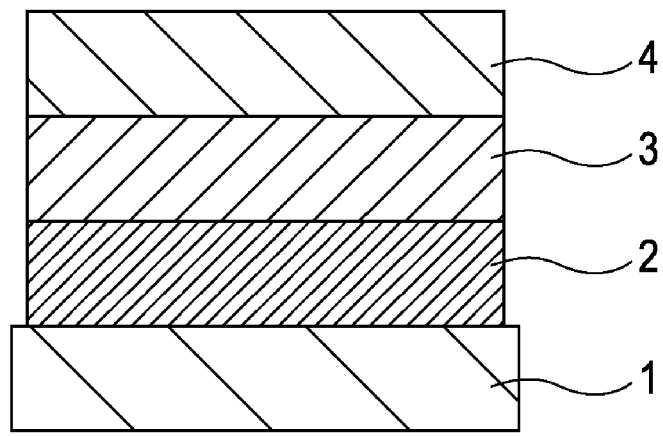
FIG. 1 is a sectional view showing an organic light-emitting device according to an embodiment of the present invention.

The present invention will be described in detail below.

The present invention relates to an organic light-emitting device including a pair of electrodes including an anode and a cathode, and a layer composed of an organic compound and spaced between the pair of electrodes. The layer composed of the organic compound contains a compound represented by the general formula [1] below.

First, the compound represented by the general formula [1] is described.

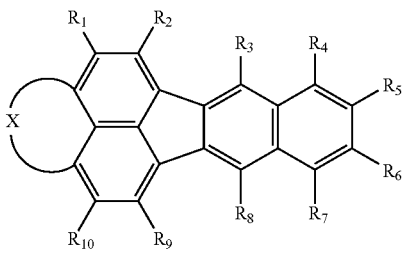

[1]

Specific examples of $R_1$ to $R_{10}$ in the general formula [1] are described below. However, these examples are only typical examples, and the present invention is not limited thereto. $R_1$ to $R_{10}$ are each (a) a hydrogen atom, (b) a halogen atom, (c) a substituted amino group, (d) a linear, branched, or cyclic alkyl group, a linear, branched, or cyclic alkyl group (in which at least one methylene group is substituted by an alkoxy or vinylene group and in which a hydrogen atom is substituted by a fluorine atom), (e) an aryl group which may be substituted, or (f) a heterocyclic group which may be substituted.

Examples of a halogen atom include a fluorine atom, a chlorine atom, and a bromine atom. When the device is formed by a vacuum deposition method, a fluorine atom is preferred.

Examples of a linear, branched, or cyclic alkyl group having 1 to 20 carbon atoms (in the alkyl group, one or at least two separate methylene groups may be substituted by —O—, and a hydrogen atom may be substituted by a fluorine atom) include a methyl group, an ethyl group, a n-propyl group, an isopropyl group, a n-butyl group, a tert-butyl group, an octyl group, a cyclohexyl group, a trifluoromethyl group, a methoxy group, and an ethoxy group.

From the viewpoint of conductivity and glass transition temperature, a methyl group, a tert-butyl group, and a trifluoromethyl group are preferred, and a methyl group and a tert-butyl group are more preferred.

Examples of an aryl group and a heterocyclic group which may be substituted include a phenyl group, a biphenyl group, a terphenyl group, a fluorenyl group, a naphthyl group, a fluoranthenyl group, an anthryl, a phenanthryl, a pyrenyl group, a tetracenyl group, a pentacenyl group, a triphenylenyl group, a perylenyl group, a thienyl group, a pyrrolyl group, a pyridyl group, a pyrazyl group, a pyrimidyl group, a pyridazinyl group, a quinolinyl group, an isoquinolinyl group, a phenanthridinyl group, an acridinyl group, a naphthyridinyl group, a quinoxalinyl group, a quinazolinyl group, a cinnolinyl group, a phthalazinyl group, a phenanthrolyl group, a phenazinyl group, a dibenzofuranyl group, a dibenzothiophenyl group, a carbazolyl group, a benzofuranyl group, a benzothiophenyl group, an indolyl group, a cycloazyl group, a benzoimidazolyl group, a benzothiazolyl group, and a benzothiadiazolyl group.

When the molecular weight of a material is very high, the sublimation temperature may be unduly increased which increases the possibility of thermal decomposition during vacuum deposition. From the viewpoint of preventing decomposition during sublimation, a phenyl group, a fluorenyl group, a naphthyl group, and a pyridyl group are preferred, and a phenyl group and a pyridyl group are more preferred.

Preferred examples of substituents which may be contained in an aryl group and a heterocyclic group include, but are not limited to, a halogen atom, a linear, branched, or cyclic alkyl group, a linear, branched, or cyclic alkyl group in which a hydrogen atom is substituted by a fluorine atom, an alkoxyl group, and a substituted amino group.

The substituents are not particularly limited, but a fluorine atom, a trifluoromethyl group, a methyl group, an ethyl group, a tert-butyl group, a methoxy group, a diphenylamino group, and a di-tert-butylamino group are preferred from the viewpoint of glass transition temperature and sublimability. Among these groups, a fluorine atom, a trifluoromethyl group, a methyl group, and a tert-butyl group are more preferred, and a methyl group and a tert-butyl group are still more preferred.

X is preferably an alkylene group having 2 to 6 carbon atoms, and the number of atoms is more preferably 2 or 3. In the alkylene group, one or two separate methylene groups may be substituted by —O—, —CO—, —CO—O—, —S—, —$NRa_1$— ($Ra_1$ may be a hydrogen atom or substituted by a linear, branched, or cyclic alkyl group having 1 to 10 carbon atoms (in the alkyl group, a hydrogen atom may be substituted by a fluorine atom), and a hydrogen atom may be substituted by a linear, branched, or cyclic alkyl group having 1 to 10 carbon atoms (in the alkyl group, a hydrogen atom may be substituted by a fluorine atom), an aryl group which may be substituted, a heterocyclic group which may be substituted, or a fluorine atom.

The constituent unit of the alkylene group is preferably —$CRa_2Ra_3$— ($Ra_2$ and $Ra_3$ are each a hydrogen atom, a halogen atom, a linear, branched, or cyclic alkyl group having 1 to 10 carbon atoms (in the alkyl group, a hydrogen atom may be substituted by a fluorine atom), more preferably a hydrogen atom, a fluorine atom, a methyl group, a tert-butyl group, or a trifluoromethyl group, and most preferably a fluorine atom, a hydrogen atom, or a trifluoromethyl group), —O—, —CO—O—, —O—CO—, —$NRa_1$— ($Ra_1$ is preferably a hydrogen atom or a linear, branched, or cyclic alkyl group having 1 to 10 carbon atoms (in the alkyl group, a hydrogen atom may be substituted by a fluorine atom), more preferably a methyl group, a tert-butyl group, or a trifluoromethyl group, and most preferably a methyl group or a trifluoromethyl group), or —CO—. Among these, —$CRa_2Ra_3$— and —O— are more preferred, and —$CRa_2Ra_3$— is most preferred.

The reason why X is particularly preferably —CRa₂Ra₃— is described below. When substituents are introduced into Ra₂ and Ra₃, the substituents are introduced at positions three-dimensionally projecting in the vertical direction from a π conjugation plane of the general formula [1]. As a result, intermolecular stacking can be suppressed. When the intermolecular stacking is suppressed, the following two beneficial effects can be expected:

1. The film properties are improved due to decreased crystallinity.
2. Concentration quenching (a phenomenon in which luminous efficiency decreases as the concentration of a guest material in a light-emitting device increases) is suppressed.

These effects are increased as the substituents introduced into Ra₂ and Ra₃ are three-dimensionally bulky or sterically hindered.

The substituents which may be contained in the general formula [1] have been described above. However, among specific structures formed by these substituents, a structure formed by only carbon atoms and hydrogen atoms is particularly preferred. This is because in a molecule composed of a hydrocarbon, contamination with ionic impurities is decreased, and thus an increase in life time of a light-emitting device can be expected, as compared with a compound containing a heteroatom having a lone electron. The contamination with ionic impurities is considered as a cause of deterioration in electric conduction of an electroluminescence device.

When a polymer compound is used in a device, it is difficult to remove impurities in a polymer, and thus the device is easily contaminated with impurities which decreases the life time of the device. However, the compound represented by the general formula [1] of the present invention is non-polymeric, and thus impurities can be easily removed by an appropriate purification method, such as recrystallization, column chromatography, or sublimation purification. Therefore, an improvement of durability of the organic light-emitting device can be expected.

The present invention can be applied to an organic light-emitting device including a pair of electrodes including an anode and a cathode and at least one layer composed of an organic compound and spaced between the pair of electrodes. In this case, when a plurality of layers composed of the organic compounds is present, any one of the layers composed of the organic compounds is a luminescent layer.

When the compound of the present invention is used as a guest material in the luminescent layer, the content of the compound is preferably 0.1% to 50% and, more preferably, 0.1% to 20%.

When the compound of the present invention is used as a host material in the luminescent layer, its content is preferably 50% to 99.9% and, more preferably, 80% to 99.9%.

When the compound represented by the general formula [1] of the present invention is used as a host material in the luminescent layer, the guest material is not particularly limited but is preferably a fluorescent material.

An organic layer containing the compound represented by the general formula [1] can be formed by conventional technique such as vacuum deposition, casting, coating, spin coating, an ink jet method, or the like.

Specific structural formulae of light-emitting device materials used in the present invention are given below. However, only typical examples are shown, and the present invention is not limited to these examples.

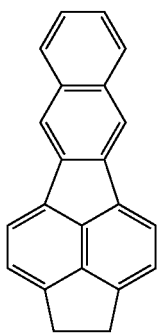

c-1

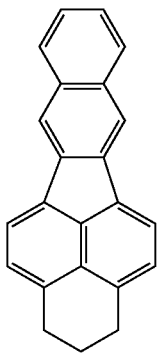

c-2

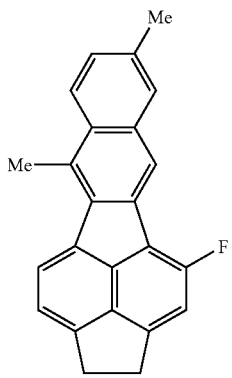

c-3

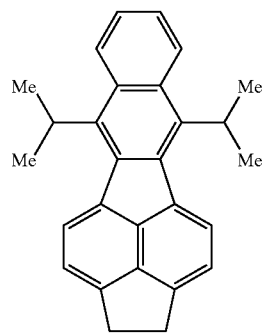

c-4

-continued
c-5
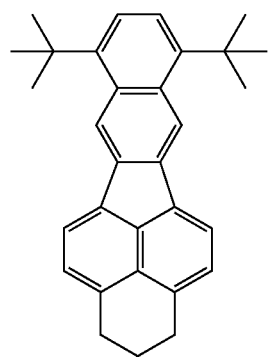
c-6
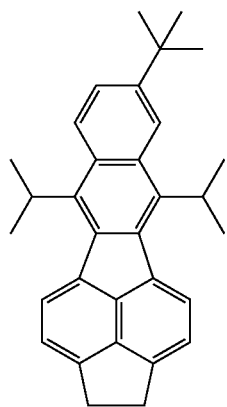
c-7
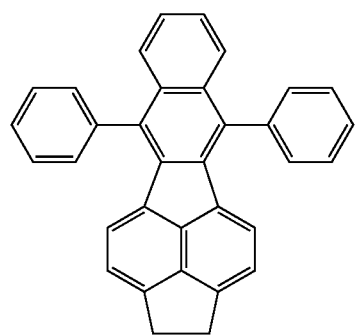
c-8
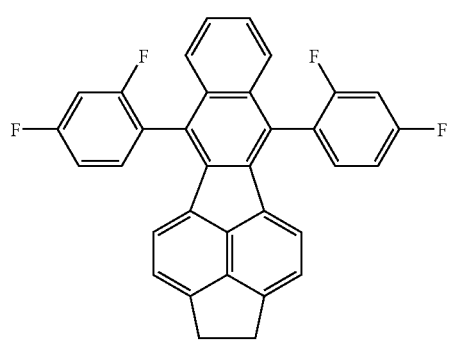
c-9
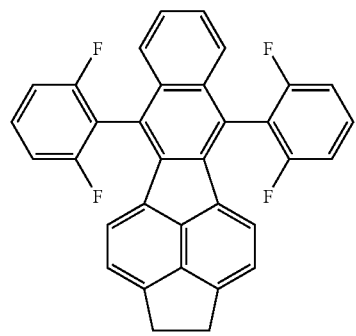
c-10
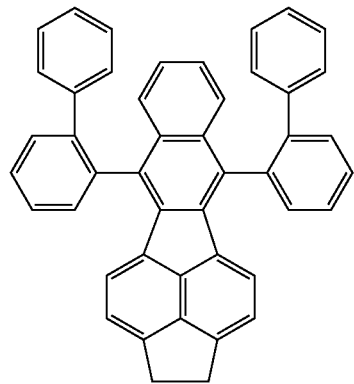
c-11
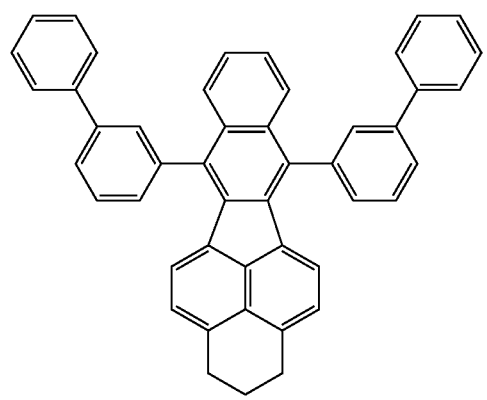
c-12
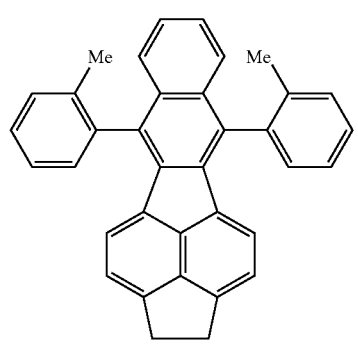

-continued
c-13
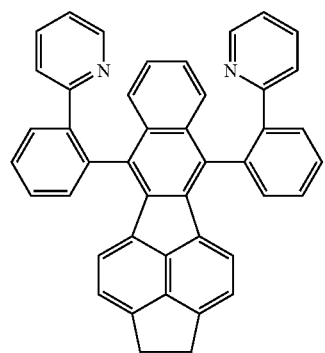
c-14
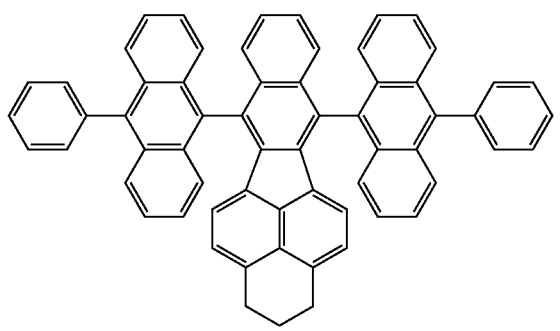
c-15
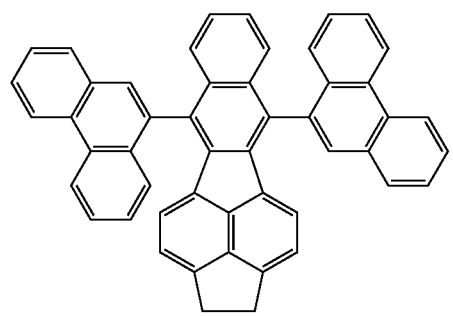
c-16
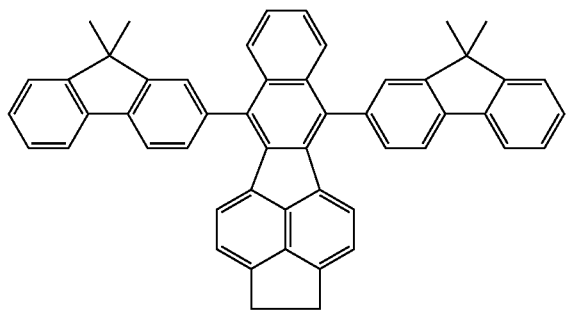
c-17
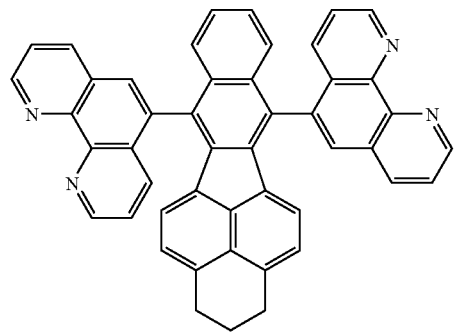
c-18
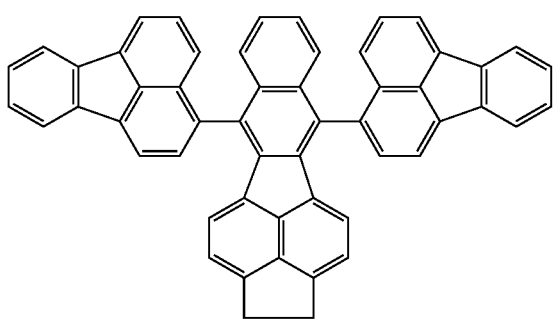
c-19
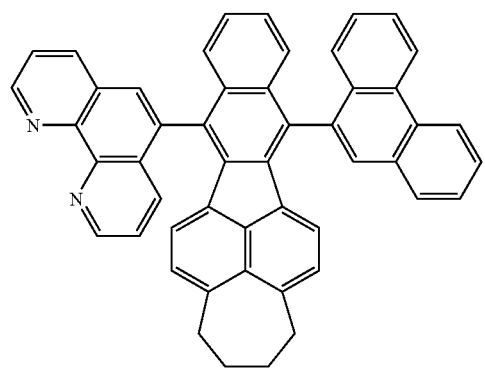
c-20
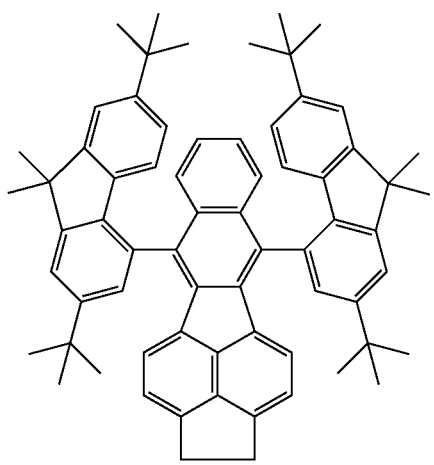

-continued
c-21
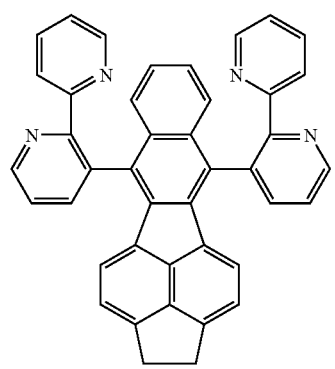
c-22
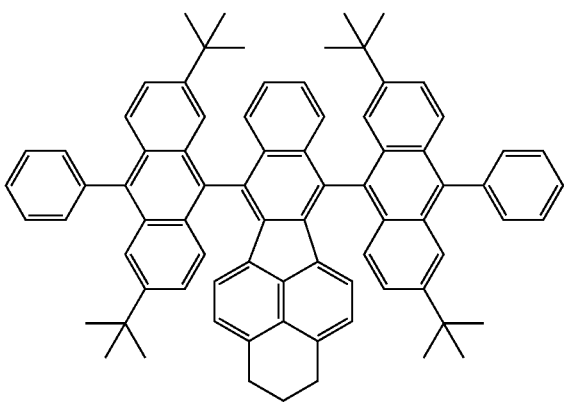
c-23
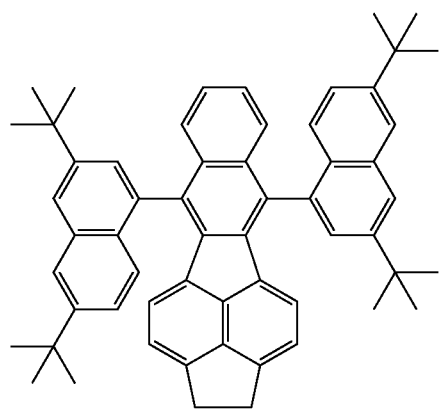
c-24
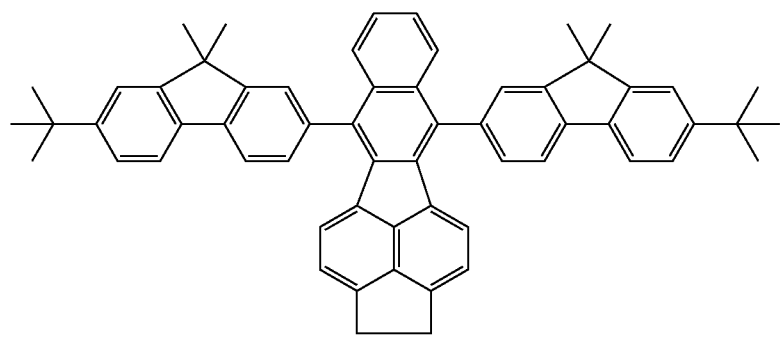
c-25
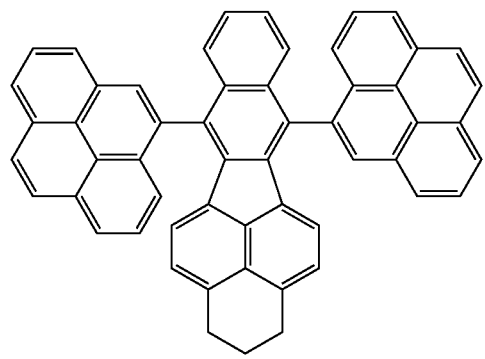
c-26
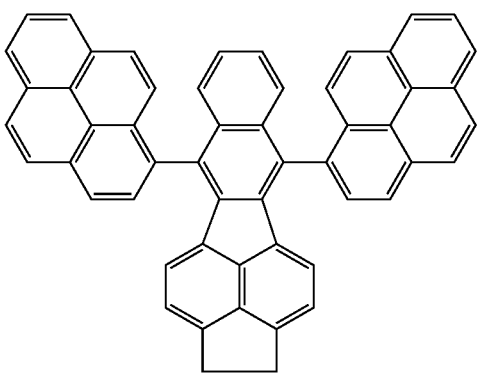

-continued
c-27
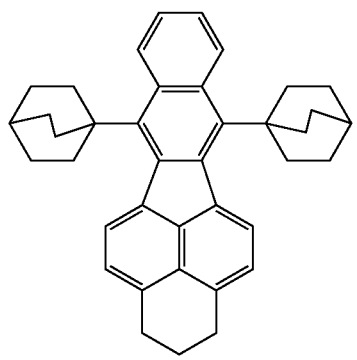
c-28
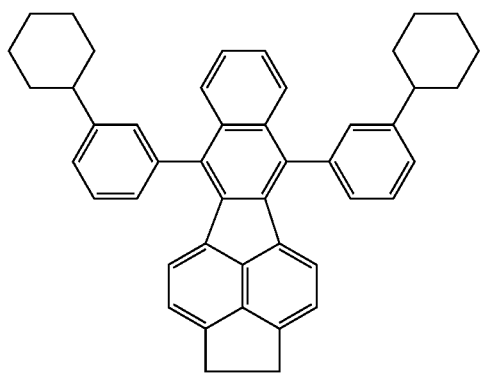
c-29
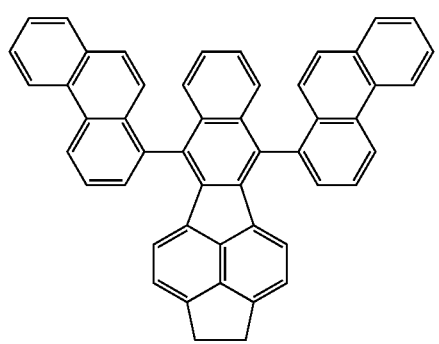
c-30
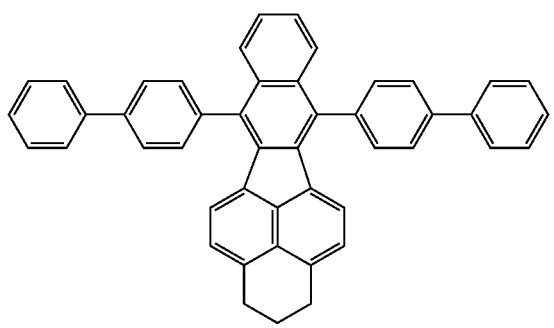
c-31
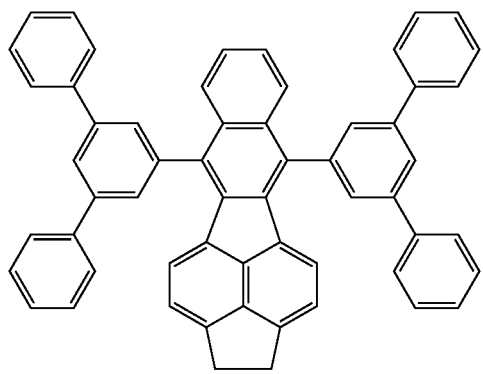
c-32
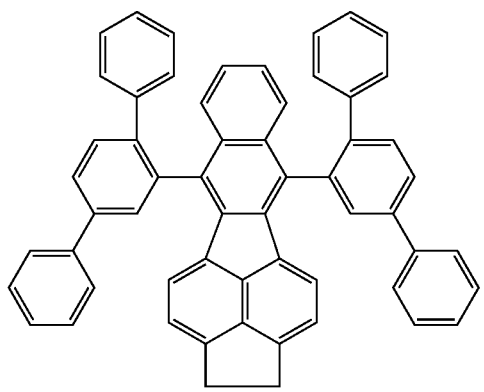
c-33
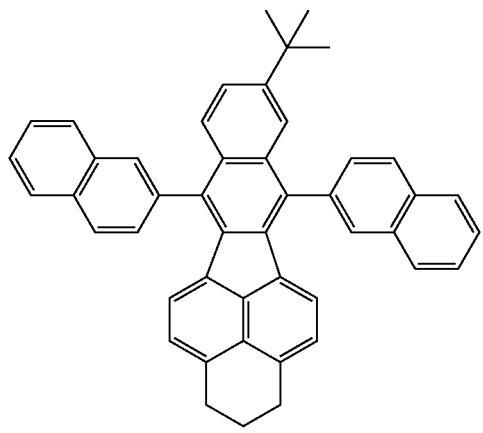
c-34
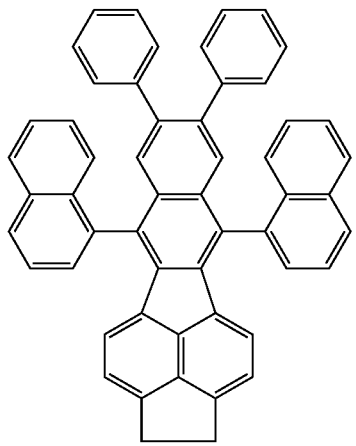

c-35
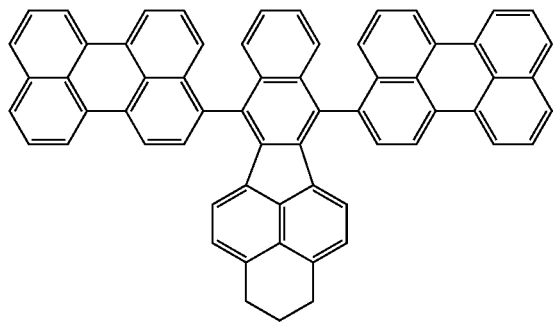
c-36
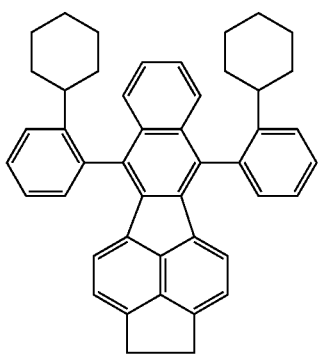
c-37
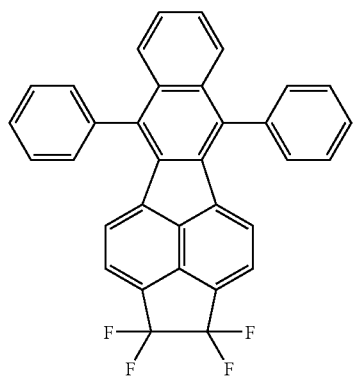
c-38
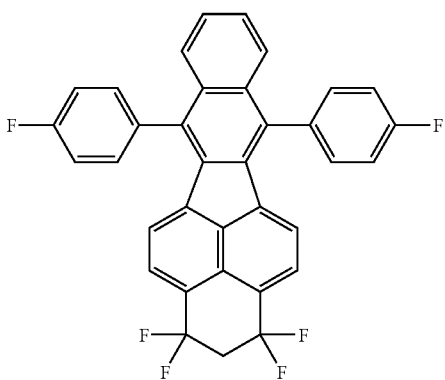
c-39
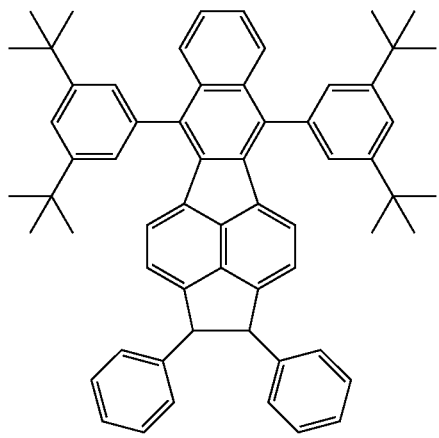
c-40
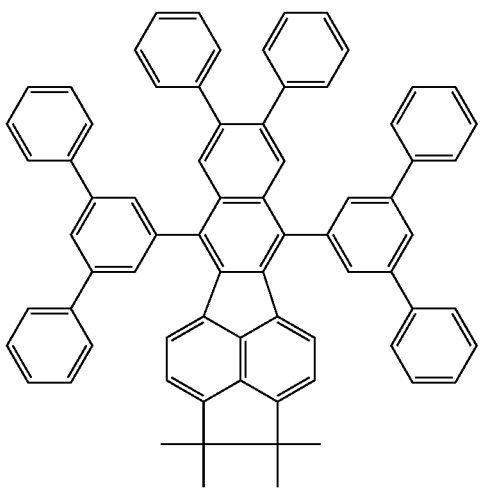

-continued
c-41
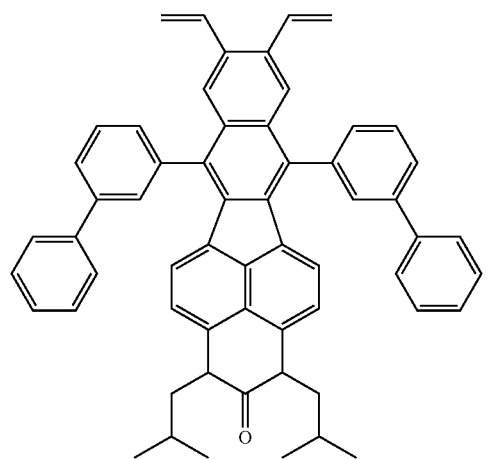
c-42
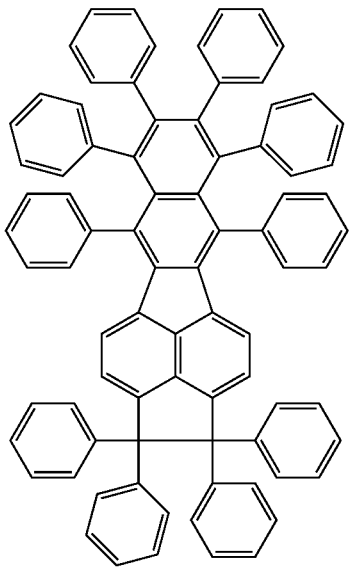
c-43
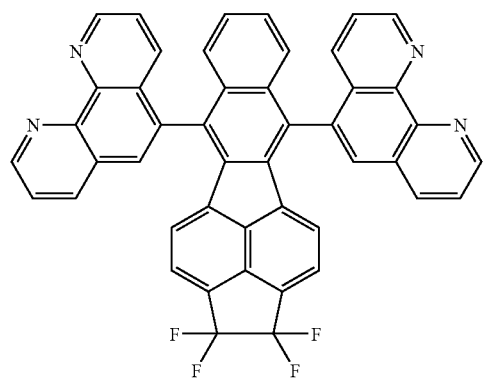
c-44
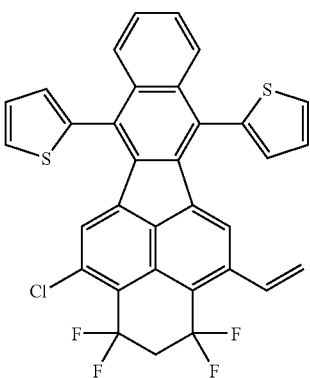
c-45
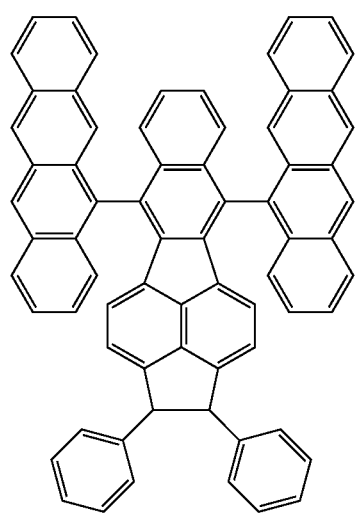
c-45
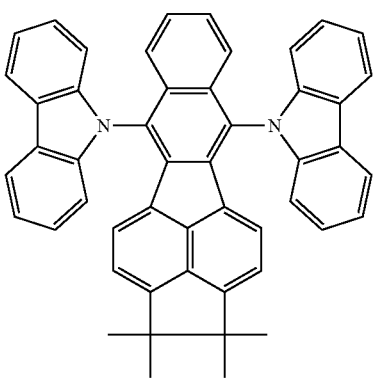

-continued
c-46
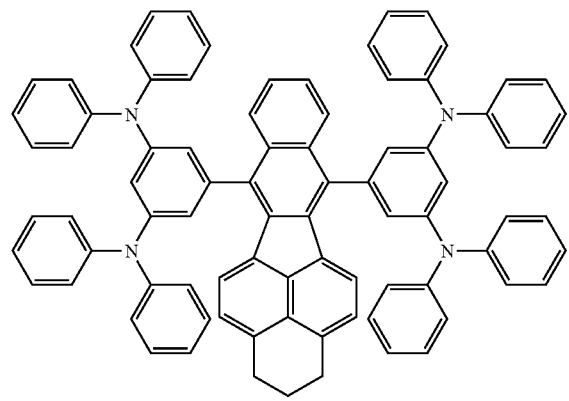
c-47
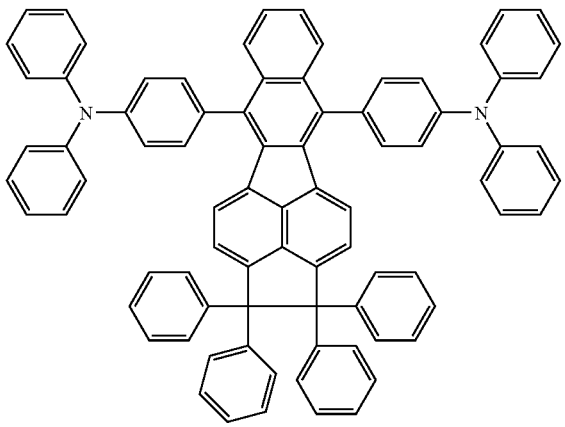
c-48
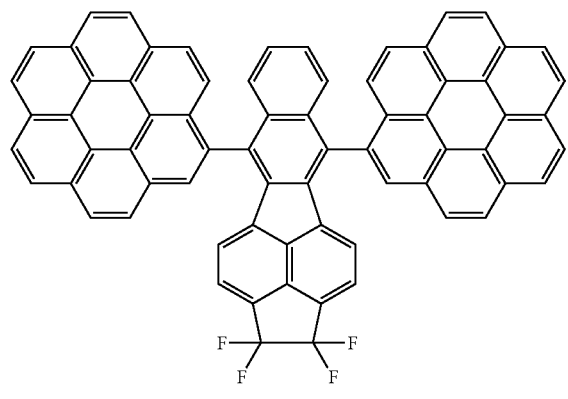
c-49
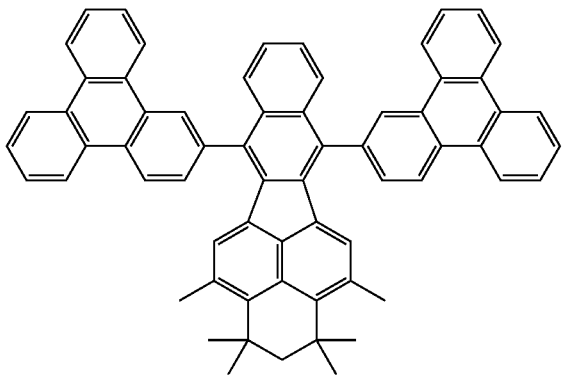
c-50
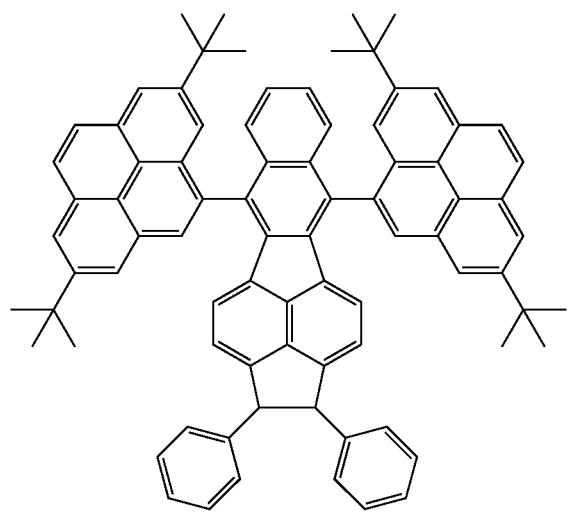
c-51
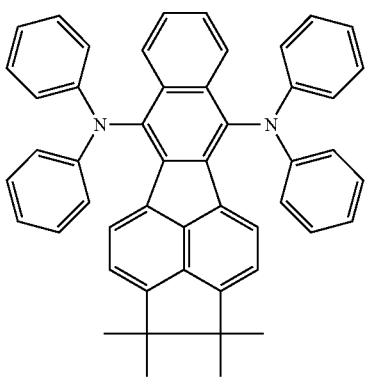

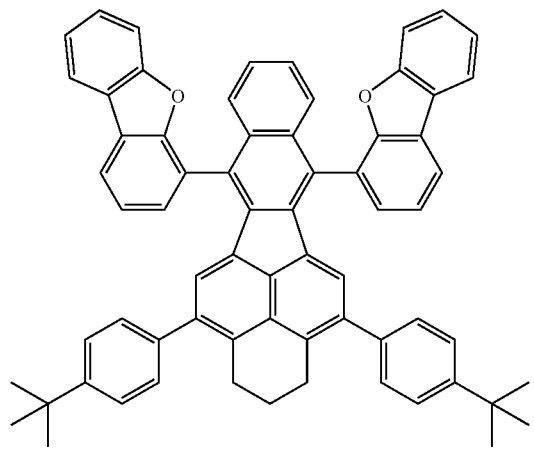
c-52
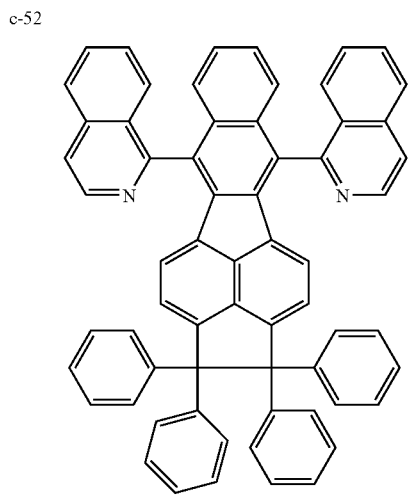
c-53
When any one of the examples has isomers due to the rotational barrier of a substituent, one or a mixture of the isomers can be used.
These compounds can be synthesized by, for example, the route described below. However, the synthesis method is not limited to this route and other conventional routes may be used.

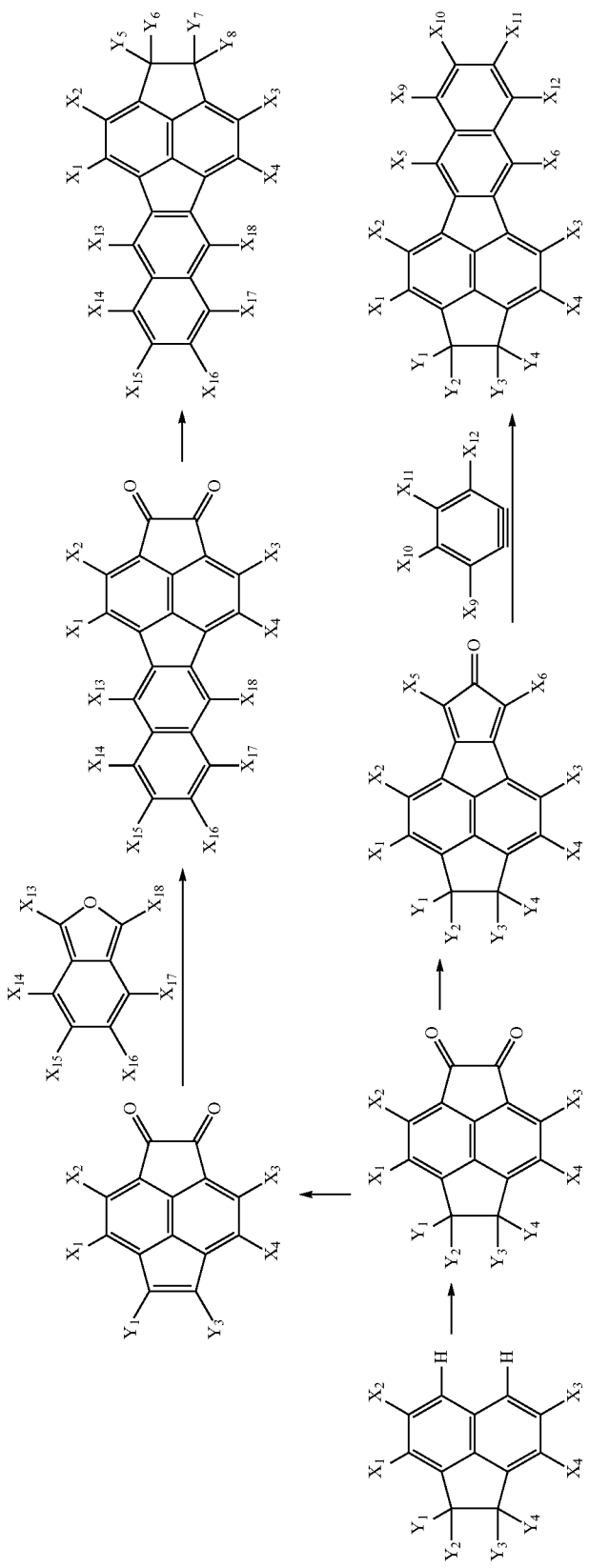

Next, the light-emitting device of the present invention is described.

The organic light-emitting device of the present invention includes the pair of electrodes including an anode and a cathode, and the layer composed of an organic compound and between the pair of electrodes, the layer composed of the organic compound containing a compound represented by the general formula [1] below. More specifically, the layer composed of the organic compound is a luminescent layer.

The organic light-emitting device of the present invention may further include another organic compound layer.

FIGS. 1 to 6 each show a light-emitting device according to a preferred embodiment of the present invention.

First, reference numerals in the drawings are described. Reference numeral 1 denotes a substrate; reference numeral 2, an anode; reference numeral 3, a luminescent layer; reference numeral 4, a cathode; reference numeral 5, a hole transport layer; reference numeral 6, an electron transport layer; reference numeral 7, a hole injection layer; and reference numeral 8, a hole/exciton blocking layer.

FIG. 1 is a sectional view showing an organic light-emitting device according to an embodiment of the present invention. As shown in FIG. 1, the anode 2, the luminescent layer 3, and the cathode 4 are provided on the substrate 1 in that order. The light-emitting device shown in FIG. 1 is useful for an embodiment in which a single compound having a hole transporting ability, an electron transporting ability, and a light emitting ability is used or a mixture of compounds having such respective characteristics is used.

Figure 2:
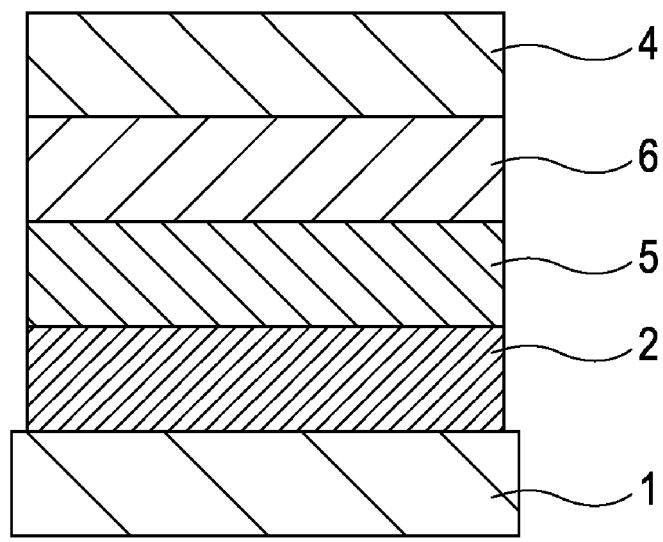
FIG. 2 is a sectional view showing an organic light-emitting device according to another embodiment of the present invention.

FIG. 2 is a sectional view showing an organic light-emitting device according to another embodiment of the present invention. As shown in FIG. 2, the anode 2, the hole transport layer 5, the electron transport layer 6, and the cathode 4 are provided on the substrate 1 in that order. This organic light-emitting device is useful for an instance in which a material having either or both of the hole transporting function and the electron transporting function is also a luminescent material. Such a material is used typically in one or both of the hole transport layer 5 and the electron transport layer 6 and is combined with a hole transporting or electron transporting material without luminescence. In this case, the luminescent layer 3 is either the hole transport layer 5 or the electron transport layer 6 whichever contains the luminescent material also having a transport function.

Figure 3:
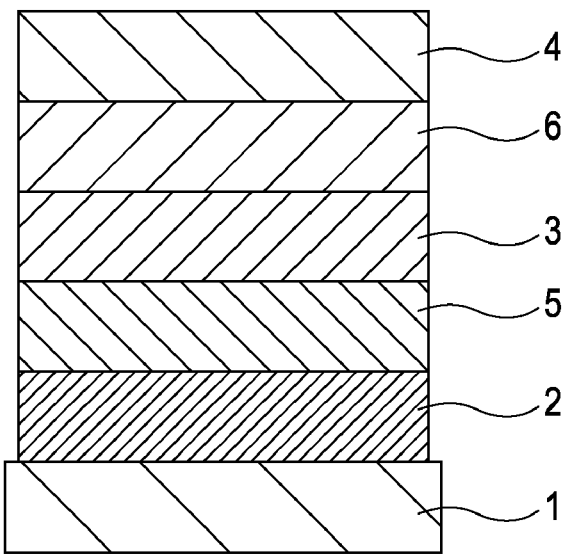
FIG. 3 is a sectional view showing an organic light-emitting device according to still another embodiment of the present invention.

FIG. 3 is a sectional view showing an organic light-emitting device according to a further embodiment of the present invention. As shown in FIG. 3, the anode 2, the hole transport layer 5, the luminescent layer 3, the electron transport layer 6, and the cathode 4 are provided on the substrate 1 in that order. In this case, the carrier transporting function and the light emitting function are separated, and compounds having a hole transporting function, an electron transporting function, and the light emitting function are appropriately combined, thereby significantly increasing the degree of freedom of material selection. In addition, various compounds having different emission wavelengths can be used, and thus luminescent hue can be diversified.

Further, the luminous efficiency can be improved by effectively enclosing carriers or excitons in the central luminescent layer.

Figure 4:
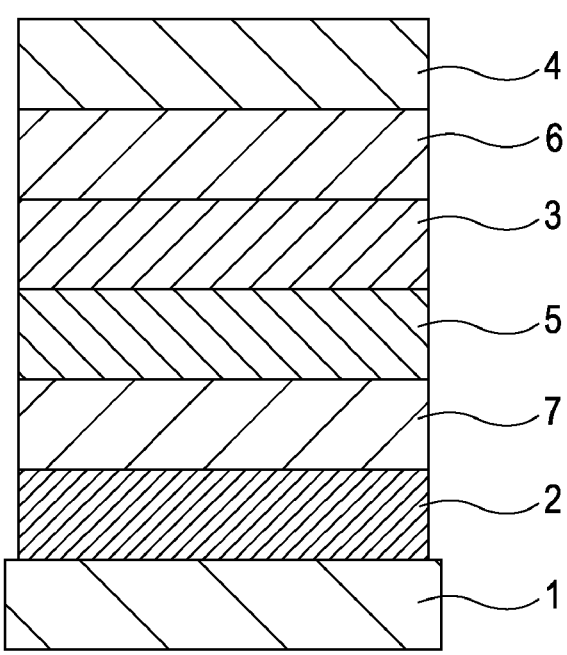
FIG. 4 is a sectional view showing an organic light-emitting device according to a further embodiment of the present invention.

FIG. 4 is a sectional view showing an organic light-emitting device according to a still further embodiment of the present invention. As shown in FIG. 4, the hole injection layer 7 is inserted on the anode side shown in FIG. 3. This embodiment has the effect of improving adhesion between the anode and the hole transport layer or improving the hole injection performance and is effective in decreasing the voltage.

Figure 5:
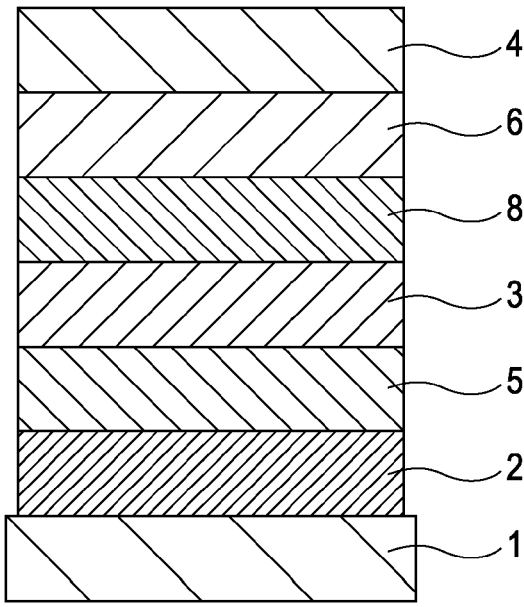
FIG. 5 is a sectional view showing an organic light-emitting device according to a still further embodiment of the present invention.
Figure 6:
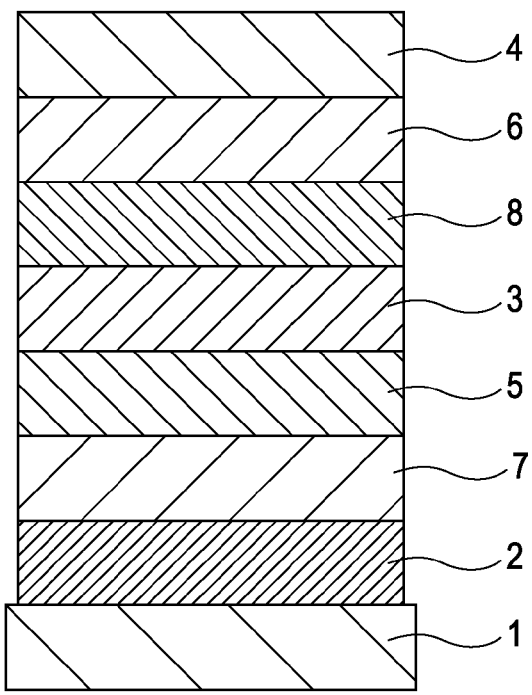
FIG. 6 is a sectional view showing an organic light-emitting device according to a further embodiment of the present invention.

FIGS. 5 and 6 are sectional views each showing an organic light-emitting device according to a further embodiment of the present invention. As shown in FIGS. 5 and 6, a layer (the hole blocking layer 8) for inhibiting the passage of holes or excitons to the cathode side is inserted between the luminescent layer and the electron transport layer shown in FIGS. 3 and 4, respectively. Such a constitution is effective in improving the luminous efficiency when a compound having a very high ionization potential is used for the hole blocking layer 8.

However, FIGS. 1 to 6 show only basic device constitutions, and the constitution of the organic light-emitting device using the compound of the present invention is not limited thereto. For example, an insulating layer may be provided at an interface between an electrode and an organic layer, or an adhesive layer or an interference layer may be provided. The hole transport layer may have multilayers including layers having different ionization potentials. Other types of layer structures, such as a layer structure including an electron transport layer formed as a multilayer of an organic material layer and a layer formed by codeposition of alkali metal ions or alkali metal salt on the organic material layer, can be used.

The compound represented by the general formula [1] of the present invention can be used in any one of the embodiments shown in FIGS. 1 to 6.

EXAMPLES

The present invention will be described in detail below with reference to examples. However, the present invention is not limited to these examples.

Synthesis Example 1

Synthesis of Exemplified Compound c-7

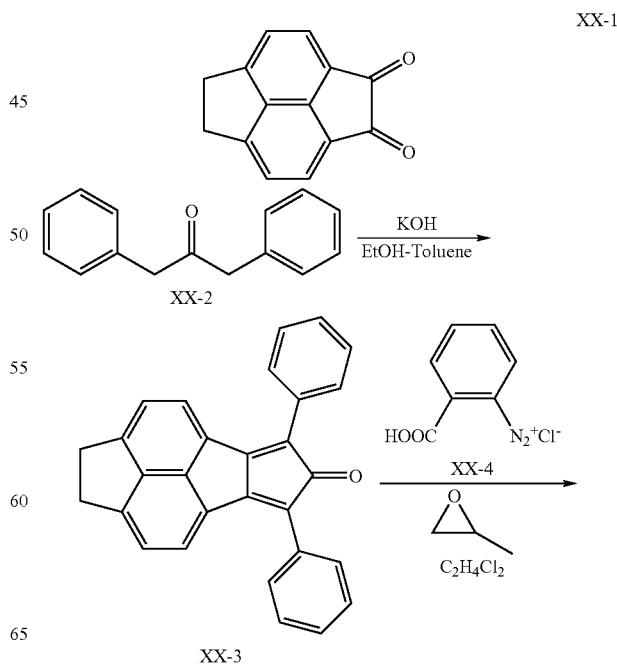

-continued

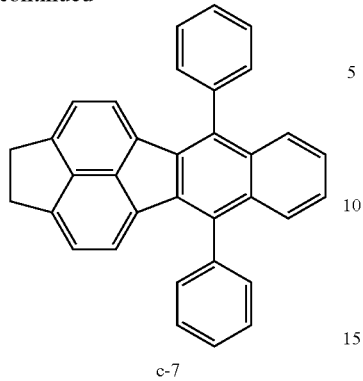

c-7

In a 20-mL reaction vessel, XX-1 (0.5 g, 2.4 mmol) and XX-2 (0.5 g, 2.4 mmol) which were synthesized according to Journal of American Chemical Society, 91, 918 (1969) and a mixed solvent (8 mL) containing toluene and ethanol at 10:1 (w/w) were added. Then, a 6N aqueous potassium hydroxide solution (1 mL) was slowly added dropwise to the resultant solution under stirring. The solution was heated to 75° C. and stirred at the same temperature for 10 minutes. After cooling to room temperature, the precipitated crystal was filtered off and washed with water and methanol to obtain XX-3 (0.8 g, yield=86%).

Next, in a 50-mL reaction vessel, XX-3 (0.8 g, 2.1 mmol), dichloroethane (16 mL), XX-4 (0.4 g, 2.3 mmol), and propylene oxide (0.5 g, 8.3 mmol) were added, followed by stirring at 70° C. for 1 hour.

The reaction solution was concentrated, and the reaction product was separated and purified by silica gel column chromatography (mobile phase:chloroform:hexane=1:2) and recrystallized from chloroform-ethanol to obtain a yellow powder of c-7 (0.7 g, 1.56 mmol, yield=75%).

The structure of the product was confirmed by a nuclear magnetic resonance apparatus (Bruker AVANCE 500 NMR Spectrometer) and a MALDI-TOF-MS mass spectrometer (Bruker AUTOFLEX).

MS (MALDI): 430.2

$^1$H NMR (CDCl$_3$, 500 MHz) δ (ppm): 7.70-7.59 (m, 12H), 7.39 (m, 2H), 7.15 (d, 2H, J=7.0 Hz), 6.65 (d, 2H, J=7.0 Hz), 3.43 (s, 4H).

The emission spectrum of this compound shows λmax=452 nm and is suitable for a blue luminescent material used for displays.

Synthesis Example 2

Synthesis of Exemplified Compound c-37

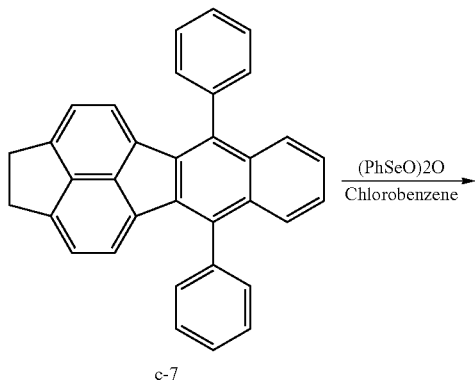

c-7

-continued

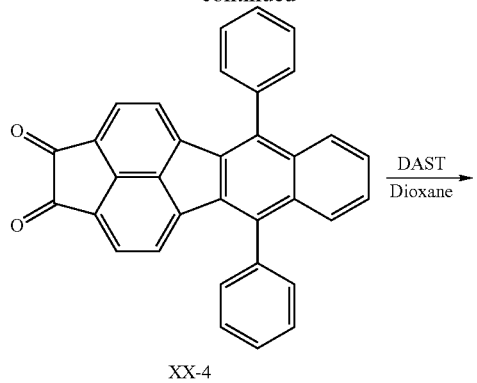

XX-4

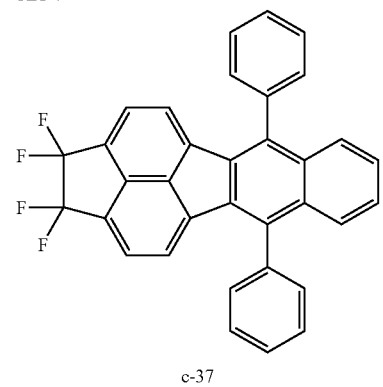

c-37

In a 300-mL reaction vessel, c-7 (3.0 g, 6.97 mmol) and chlorobenzene (150 ml) were added. Then, benzene boronic anhydride (70%) (7.15 g, 13.9 mmol) was added to the mixture, following by heating to 130° C. and stirring at the same temperature for 24 hours.

The reaction solution was concentrated, the reaction product was separated and purified by silica gel column chromatography (mobile phase:chloroform:hexane=1:1) to obtain a yellow powder XX-4 (3.0 g, 6.54 mmol, yield=93%).

In a 50-mL pressure-proof test tube, XX-4 (1.0 g, 2.18 mmol) and anhydrous dioxane (15 ml) were added. Then, diethylaminosulfur trifluoride (DAST) (90%) (2.34 g, 13.1 mmol) was added to the resultant mixture, followed by heating to 100° C. and stirring at the same temperature for 14 hours. After cooling to room temperature, diethylaminosulfur trifluoride (DAST) (90%) (2.34 g, 13.1 mmol) was further added to the resultant mixture, followed by heating to 100° C. and stirring at the same temperature for 5 hours.

After cooling to room temperature, the reaction solution was poured into saturated sodium bicarbonate water (80 mL), and the precipitated crystal was filtered off. The crystal was separated and purified by silica gel column chromatography (mobile phase:chloroform:hexane=1:1) to obtain a yellow powder of c-37 (731 mg, 1.45 mmol, yield=66%).

The structure of the product was confirmed by a nuclear magnetic resonance apparatus (Bruker AVANCE 500 NMR Spectrometer) and a MALDI-TOF-MS mass spectrometer (Bruker AUTOFLEX).

MS (MALDI): 502.1

$^1$H NMR (CDCl$_3$, 500 MHz) δ (ppm): 7.72-7.66 (m, 8H), 7.60-7.56 (m, 6H), 7.47 (m, 2H), 6.76 (d, 2H, J=7.2 Hz). The emission spectrum of this compound shows λmax=444 nm and is suitable for a blue luminescent material used for displays.

Example 1

A device including three organic layers as shown in FIG. 3 was manufactured.

ITO (transparent electrode 2) of 100 nm was patterned on a glass substrate (transparent substrate 1). Then, organic layers and electrode layers, which will be described below, were continuously deposited on the ITO substrate by resistance-heating vacuum deposition in a vacuum chamber of 10$^{-5}$ Pa so that the opposing area between electrodes was 3 mm$^2$.

Hole transport layer (5) (40 nm): α-NPD
Luminescent layer (3) (30 nm): HOST-1: Exemplified Compound c-7 (weight ratio 5%)
Electron transport layer (6) (30 nm): Bphen (manufactured by Dojindo Laboratories)
Metal electrode (4-1) (1 nm): KF
Metal electrode (4-2) (130 nm): Al

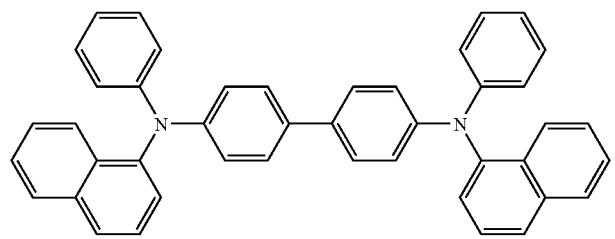

α-NPD

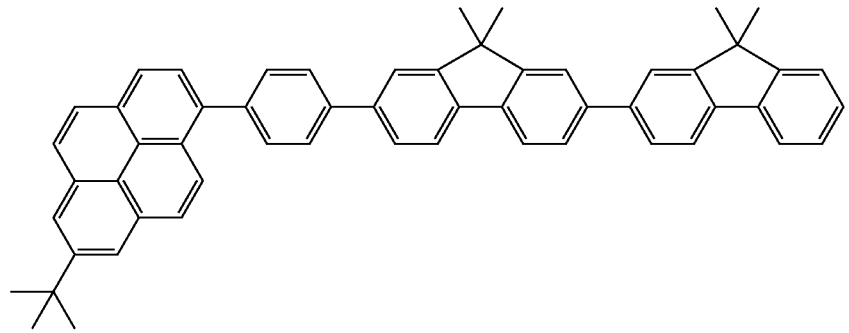

HOST-1

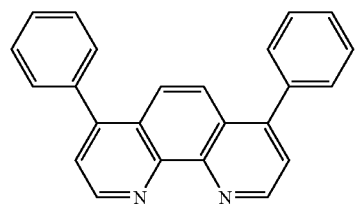

BPhen

With respect to the characteristics of the organic light-emitting device, current-voltage characteristics were measured by a microammeter 4140B manufactured by Hewlett-Packard, and luminance was measured by BM7 manufactured by Topcon Corporation. In the device of this example, blue light emission of 600 cd/m² was confirmed when a voltage of 5 V was applied.

Also, when a voltage was applied to the device of this example for 50 hours in a nitrogen atmosphere, the continuation of sufficient emission was confirmed. It was also confirmed that the light-emitting device using c-7 as a guest material is useful as a blue light-emitting device.

Example 2

A device was formed by the same method as in Example 1 except that Exemplified Compound c-37 was used in place of Exemplified Compound c-7 used in Example 1. In the device of this example, blue light emission of 400 cd/m² was confirmed when a voltage of 6 V was applied.

Also, when a voltage was applied to the device of this example for 50 hours in a nitrogen atmosphere, the continuation of sufficient emission was confirmed. It was also confirmed that the light-emitting device using c-37 as a guest material is useful as a blue light-emitting device.

While the present invention has been described with reference to exemplary embodiments, it is to be understood that the invention is not limited to the disclosed exemplary embodiments. The scope of the following claims is to be accorded the broadest interpretation so as to encompass all modifications and equivalent structures and functions.

This application claims the benefit of Japanese Application No. 2007-063596 filed Mar. 13, 2007, which is hereby incorporated by reference herein in its entirety.

What is claimed is:

1. An organic light-emitting device comprising:
a pair of electrodes including an anode and a cathode; and
a layer of an organic compound spaced between the pair of electrodes;
wherein the layer of the organic compound contains a compound represented by the following formula:

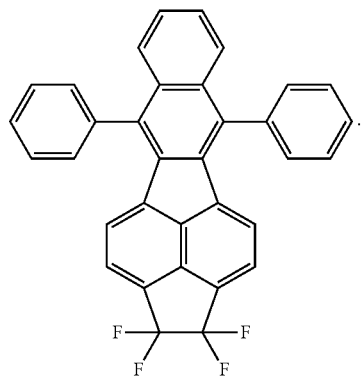

2. The organic light-emitting device according to claim 1, wherein the layer of the organic compound is a luminescent layer.

3. The organic light-emitting device according to claim 2, wherein the luminescent layer is composed of at least a host compound and a guest compound.

4. The organic light-emitting device according to claim 3, wherein the compound represented by the formula is the guest compound of the luminescent layer.

* * * * *